(12) United States Patent
DeFreez et al.

(10) Patent No.: US 6,784,990 B1
(45) Date of Patent: Aug. 31, 2004

(54) PARTICLE DETECTION SYSTEM IMPLEMENTED WITH A MIRRORED OPTICAL SYSTEM

(75) Inventors: Richard K. DeFreez, Azalea, OR (US); James Brady, Ashland, OR (US); Kenneth L. Girvin, Grants Pass, OR (US)

(73) Assignee: Pacific Scientific Instruments Company, Grants Pass, OR (US)

( * ) Notice: Subject to any disclaimer, the term of this patent is extended or adjusted under 35 U.S.C. 154(b) by 0 days.

(21) Appl. No.: 10/407,650

(22) Filed: Apr. 4, 2003

(51) Int. Cl.[7] .............................................. G01N 21/00
(52) U.S. Cl. ........................ 356/338; 356/336; 356/339
(58) Field of Search ................................ 356/336, 337, 356/338, 436

(56) References Cited

U.S. PATENT DOCUMENTS

| | | | | |
|---|---|---|---|---|
| 4,422,761 A | * | 12/1983 | Frommer | 356/338 |
| 4,984,889 A | | 1/1991 | Sommer | 356/336 |
| 5,467,189 A | * | 11/1995 | Kreikebaum et al. | 356/336 |
| 5,726,753 A | * | 3/1998 | Sandberg | 356/338 |
| 5,731,875 A | * | 3/1998 | Chandler et al. | 356/336 |
| 5,767,967 A | * | 6/1998 | Yufa | 356/336 |
| 5,805,281 A | * | 9/1998 | Knowlton et al. | 356/336 |
| 5,815,264 A | * | 9/1998 | Reed et al. | 356/336 |
| 5,999,250 A | * | 12/1999 | Hairston et al. | 356/336 |
| 6,016,194 A | | 1/2000 | Girvin et al. | 356/337 |
| 6,104,491 A | * | 8/2000 | Trainer | 356/336 |
| 6,137,572 A | * | 10/2000 | DeFreez et al. | 356/336 |
| 2001/0035954 A1 | * | 11/2001 | Rahn et al. | 356/336 |

* cited by examiner

Primary Examiner—Michael P. Staftra
Assistant Examiner—Juan D Valentin, II
(74) Attorney, Agent, or Firm—Stoel Rives LLP (57) ABSTRACT

A particle detection system exhibits an increased ability to detect the presence of submicron diameter particles and to distinguish between noise and pulse output signals generated by small diameter particles on which a light beam is incident. This increased ability results from the incorporation of a light reflector, a pair of detector elements that detect correlated portions of the light beam that have been scattered in multiple directions, and a coincidence circuit that determines whether each detector element in the pair concurrently generates a pulse output signal exceeding a predetermined threshold. Sample particles are counted only when both detector elements concurrently detect scattered light components.

19 Claims, 5 Drawing Sheets

Detection Threshold

Fig. 5

PARTICLE DETECTION SYSTEM IMPLEMENTED WITH A MIRRORED OPTICAL SYSTEM

TECHNICAL FIELD

The present invention relates to optical particle detection and, in particular, to a particle detection system with increased sensitivity in the detection of submicron diameter particles.

BACKGROUND OF THE INVENTION

Contamination control, including particle monitoring, plays a critical role in the manufacturing processes of several industries. These industries require clean rooms or clean zones with active air filtration and require the supply of clean raw materials such as process gases, deionized water, chemicals, and substrates. In the pharmaceutical industry, the Food and Drug Administration requires particle monitoring because of the correlation between detected particles in an aseptic environment and viable particles that contaminate the product being produced. Semiconductor fabrication companies require particle monitoring as an active part of quality control. As integrated circuits become more compact, line widths decrease, thus reducing the size of particles that can cause quality problems. Accordingly, it is important to detect and accurately measure submicron particles of ever-decreasing sizes and numbers per volumetric unit.

To perform particle monitoring, currently commercially available submicron particle detection systems use optical detection techniques to determine the presence, size, and number of particles in a volumetric unit. The foundation of this technology is optical scattering of a light beam and detection of the optical signal after it has been scattered by a sample particle. The standard particle detection approach, which was developed during the late 1980s, entails intersecting, in a region referred to as a "view volume," a light beam and a sample stream containing sample particles. Light scattered from the view volume is collected with optics and focused onto a detection system that collects the volume of light and projects it onto one or more detector elements. The ability of a particle detection system to detect small particles depends on its ability to distinguish between noise and pulse output signals generated from light scattered by submicron sample particles.

What is needed, therefore, is a particle detection system having high submicron particle detection sensitivity.

SUMMARY OF THE INVENTION

An object of the invention is, therefore, to provide a particle detection method and system characterized by increased submicron particle detection sensitivity and accurate particle size determination.

The particle detection system of the present invention includes a flow chamber within which a light beam and a fluid stream containing sample particles intersect to form a view volume. The incidence of a sample particle on the light beam causes portions of the light beam to scatter from the view volume in the form of first and second correlated scattered light components. The first correlated scattered light component exits the view volume in a first direction, is collected and focused by a light collection lens system, and is detected by a first detector element of a pair of detector elements located in an array of detector elements. The second correlated scattered light component exits the view volume in a second direction and is incident upon a light reflector. The light reflector reflects in an inverted state the second correlated scattered light component and focuses it into the view volume. The second correlated scattered light component then passes through the view volume, is collected and focused by the light collection lens system, and is detected by a second detector element of the pair of detector elements.

Each detector element in the pair of detector elements detects the incidence of light and generates a pulse output signal, the magnitude of which depends on the intensity of the incident scattered light component. A signal processing system performs analog or digital signal processing of only those pulse output signals that are temporally and spatially coincident such that both of the first and second detector elements of the pair of detector elements concurrently generate pulse output signals. If each of the pulse output signals concurrently crosses its associated threshold, the signal processing system filters the pulse output signals to remove noise and amplifies the signals to generate a final pulse output signal indicating the presence and size of the sample particle.

Signal enhancement results from the required temporal and spatial coincidence of pulse output signals corresponding to the same sample particle. Because sample particles are counted only when both detector elements of a pair concurrently detect a scattered light component and when the resultant pulse output signals exceed a predetermined threshold, randomly occurring noise pulses or excursions are unlikely to concurrently contact both of the detector elements in the pair. Specifically, the probability that two pulse output signals will concurrently exceed the predetermined threshold is equal to the square of the probability that an individual pulse output signal will exceed the threshold. The coincidence function permits the use of a lower threshold for a given false count rate because most noise is random and will not concurrently trigger both detector elements in the pair. Use of a lower threshold facilitates the detection of smaller sample particles.

The particle detection system also preferably includes a noise detection and cancellation system that prevents noise from triggering a coincidence event. The preferred noise detection and cancellation system includes a noise detector that is positioned to monitor only the laser beam and a cancellation unit that removes (i.e., by subtraction or division) the signal generated by the noise detector from the signal generated by each detector element.

The particle detection system of the present invention has an increased ability to distinguish between noise and low-amplitude pulse output signals caused by small diameter particles. The required temporal and spatial coincidence of pulse output signals results in signal enhancement. Because sample particles are counted only when both symmetrically opposed detector elements concurrently detect scattered light correlated components having a pulse output signal that exceeds a predetermined threshold, the incidence of randomly occurring noise pulses or excursions causing a false signal is significantly decreased. Specifically, the probability that two pulse output signals will concurrently exceed the predetermined threshold is equal to the square of the probability that an individual pulse output signal will exceed the threshold. Consequently the threshold for a given false count rate may be lowered by more than a factor of the square root of two while maintaining the desired overall false count rate. Thus the coincidence function allows the use of a lower threshold setting without increasing the incidence of false particle signals, since most noise is random and is unlikely to concurrently trigger both detector elements of a symmetrically opposed pair. The use of a lower threshold facilitates more accurate detection of smaller diameter particles.

Additional objects and advantages of this invention will be apparent from the following detailed description of preferred embodiments thereof, which proceeds with reference to the accompanying drawings.

DETAILED DESCRIPTION OF PREFERRED EMBODIMENT

The particle detection system of the present invention has an increased ability to distinguish between noise and pulse output signals generated by small particles incident upon a light beam. This increased ability results from the incorporation of a light reflector, a pair of detector elements that detect correlated portions of a light beam scattered in multiple directions by a particle, and a coincidence circuit that determines whether the detector elements in the pair concurrently generate pulse output signals exceeding a predetermined threshold. If both detector elements of the pair concurrently generate pulse output signals, there is a high probability that the signals were caused by the incidence of a sample particle on the light beam rather than by noise variations in the particle detection system. The ability of the particle detection system of the present invention to distinguish low-amplitude pulse output signals from noise enables the system to detect smaller diameter particles than those detectable by prior art particle detection systems.

Figure 1:
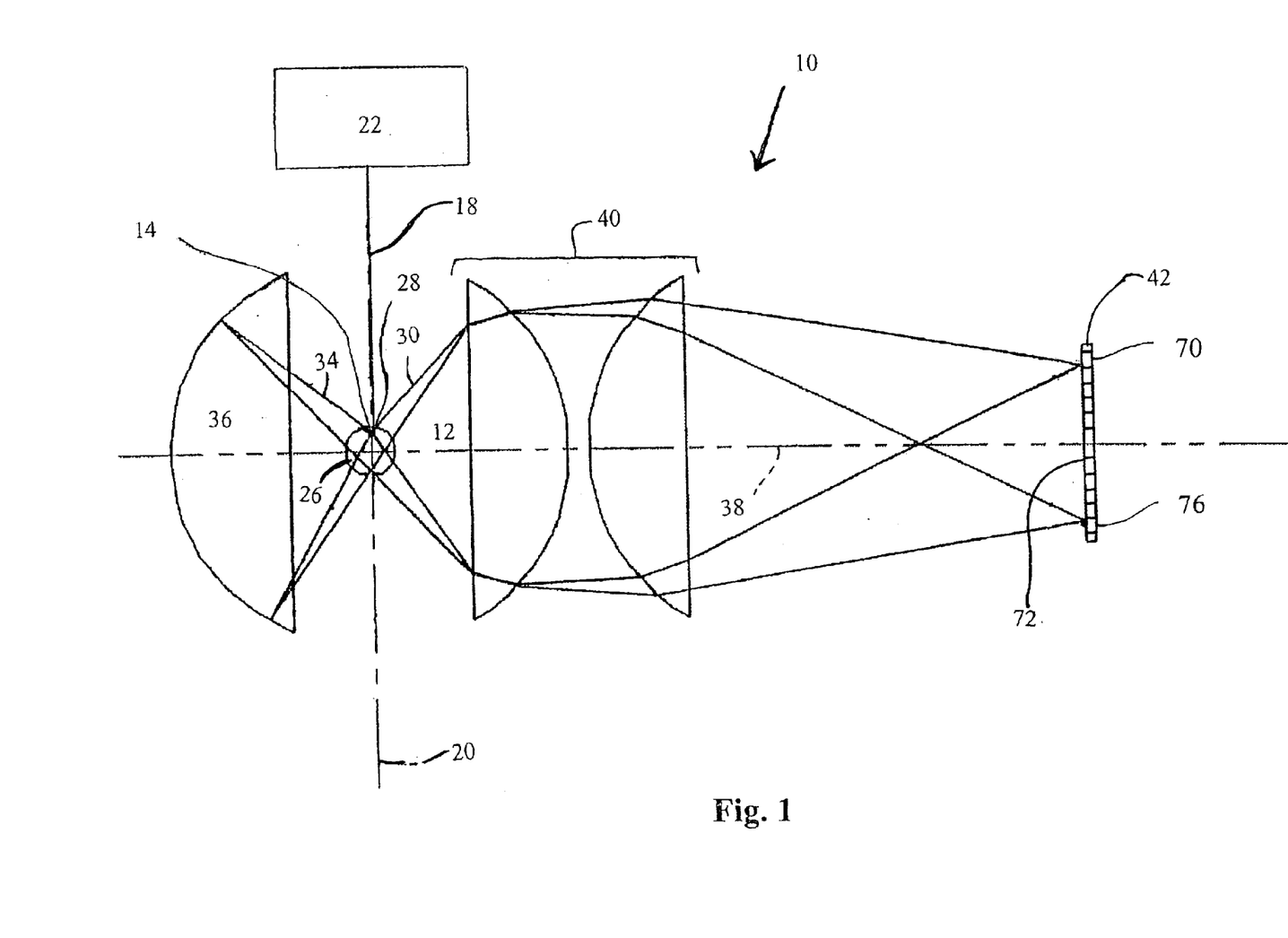
FIG. 1 is a plan view of a preferred embodiment of the particle detection system of the present invention.

FIG. 1 shows a preferred embodiment of a particle detection system 10 configured in accordance with the present invention. System 10 includes a flow chamber 12 through which a particle-carrying sample fluid stream 14, such as air, flows in a flow direction (out of the plane of FIG. 1) and a light beam 18 emitted by a light source 22 propagates in a direction along an optical axis 20. Light source 22 is preferably a diode laser that is robust, efficient, and compact. Exemplary preferred light sources are gas, dye, or solid-state lasers. Fluid stream 14 and light beam 18 intersect within the effective center of flow chamber 12 in a region called a view volume 26.

Following its incidence on a particle 28 present in view volume 26, light beam 18 scatters as components of light initially propagating in first and second generally opposite directions. In a preferred embodiment, light components 30 propagate in the first general direction and light components 34 propagate in the second general direction, reflect off and are inverted about an optical axis by a light reflecting optical element 36, and propagate back into view volume 26. Thus light reflecting optical element 36 acts as an inverting, retroreflective device. Light components 30 and 34 then propagate in a direction along a collection system axis 38 through a light collection lens system 40 that converges light components 30 and 34 on corresponding detector elements of a photodetector array 42. Because they are scattered by the same particle 28, light components 30 and 34 are correlated in that their incidence on the corresponding detector elements produces detector output signals indicative of the size of particle 28 that scattered light beam 18.

Second optical element 36 is preferably a light reflecting optical element, such as a curved light reflector having an outer surface that is coated with a high-reflectance coating. More preferably, second optical element 36 is a light reflector in the form of a curved segment with a curved outer surface that is spherically, elliptically, or aspherically shaped. Preferably, the light reflector is a mirror and is positioned opposite light collection lens system 40 with view volume 26 disposed between them. Light reflector 36 is preferably centered on collection system axis 38 such that the center of curvature of light reflector 36 is aligned with the effective center of view volume 26. Light reflected off second optical element 36 and propagating back through view volume 26 is inverted about collection system axis 38.

FIG. 1 is useful in the explanation of the processing of light components 30 and 34 formed by the incidence of light beam 18 on particle 28. The incidence of light beam 18 upon particle 28 scatters first and second correlated light components 30 and 34 from view volume 26 in, respectively, first and second directions. First light component 30 is collected by light collection lens system 40 and focused onto a first detector element 70 of photodetector array 42. Photodetector array 42 is positioned so that its light receiving surface 72 is substantially perpendicular to and the number of detector elements in the linear array is bisected by collection system axis 38. Particles struck by light beam 18 at different locations within view volume 26 will cause points of light to be focused onto photodetector array 42 in different positions corresponding to the relative locations of the particles within view volume 26.

Light collection lens system 40 collects light scattered by particles within view volume 26 and images the light onto photodetector array 42. Exemplary light collection lens systems are commonly known to those with skill in the art; however, a refractive light collection lens system is preferred.

Second light component 34 is scattered by particle 28 from view volume 26 in a second direction initially away from light collection lens system 40 and is incident upon second optical element 36, which acts as a light reflector that reflects and inverts about optical axis 20 second light component 34. As shown in FIG. 1, second light component 34 returns to view volume 26 in an inverted state at a location approximately the same distance from, but on the opposite side of, collection system axis 38 as that of first light component 30. The inverted second light component 34 propagates through view volume 26 and light collection lens system 40, which focuses the inverted second light component onto a second detector element 76 of photodetector array 42. First and second detector elements 70 and 76 constitute a related pair of detector elements of photodetector array 42 such that first detector element 70 is spatially related to the first light component 30 scattered by particle 28 and second detector element 76 is spatially related to the inverted second light component 34 scattered by particle 28.

Because of the above-described system component alignment, first and second detector elements 70 and 76 are approximately equidistant from and on opposite sides of collection system axis 38.

Photodetector array 42 is preferably a linear array of photodiode detectors having dimensions that are proportional to the image dimensions of view volume 26. An array of photodiode detectors is used for the purpose of detecting coincidence and thereby reducing noise and false counts. As stated above, collection system axis 38 divides array 42 into two sets of detector elements, one that contains first detector element 70 and another that contains second detector element 76. Detector elements 70 and 76 are preferably equidistant from collection system axis 38. Exemplary detector arrays include an avalanche photodetector (APD) array, a photomultiplier tube (PMT) array with an array of anodes, and a photodetector (PD) array. An exemplary commercially available photodetector array is the Perkin Elmer Optoelectronics Model C30985E, with 25 detector elements each measuring 0.3 mm center-to-center.

First and second detector elements 70 and 76 generate pulse output signals corresponding to, respectively, first and second correlated light components 30 and 34. The amplitude of a pulse output signal is dependent on the size of the particle to which it corresponds. Signal processing takes place downstream of photodetector array 42 and converts the pulse output signal into a voltage that can be measured. Because particle size is directly related to light amplitude, which is directly related to pulse output signal amplitude, which is directly related to voltage magnitude, the size of a particle may be determined by measuring the voltage corresponding to each pulse output signal. The signal is preferably amplified before reaching the preamplifier stage, where inherent electronic noise is added to the signal. Because the signal has already been amplified, the proportional amount of electronic noise added at the preamplifier stage is smaller than what it would have been had the signal not been amplified before reaching the preamplifier stage.

Figure 2:
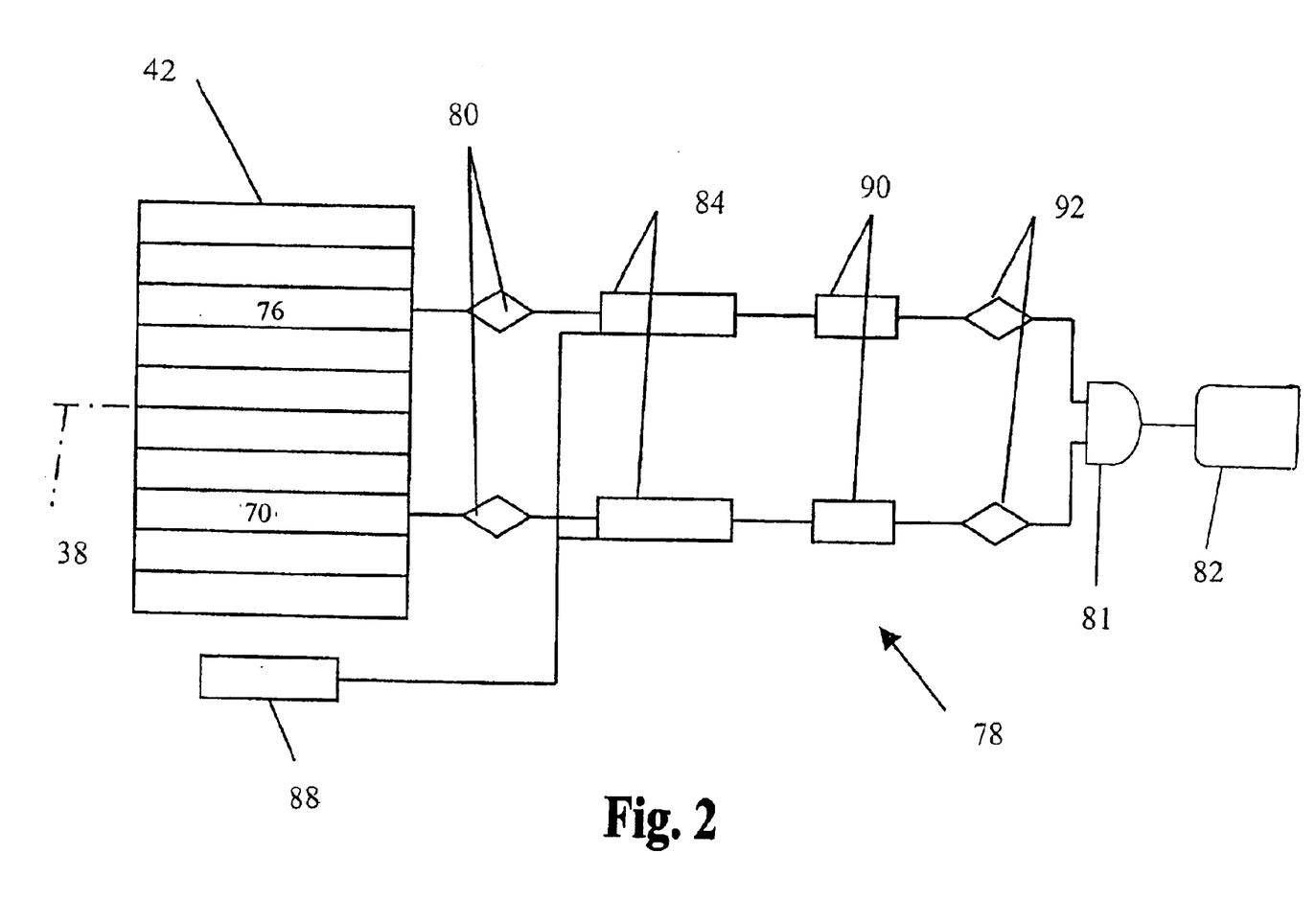
FIG. 2 is a schematic diagram of a preferred signal processing system for use with the particle detection system of the present invention.

As shown in FIG. 2, a preferred signal processing system 78 of the present invention includes a transimpedance amplifier 80 that converts from electric current to voltage the pulse output signals generated by one of first and second detector elements 70 and 76 in photodetector array 42. Next, background noise is canceled from the voltage signal at a noise cancellation unit 84 that subtracts or divides a baseline pulse measured by a noise detector 88. Noise detector 88 is preferably an end-cavity detector or a detector element that is not used to perform particle detection. Noise cancellation minimizes the incidence of false particle signals based on noise common to the light source. Division-based noise cancellation is preferable to subtractive noise cancellation because division-based cancellation is more robust and provides greater tolerance of differences in phase shift, time delay, and gain. Following noise cancellation, the pulse output signals are filtered by a filter 90, the shape of which is preferably similar to the shape of the frequency response characteristic of the pulse output signal.

Such a matched filtering approach is described in, for example, *Intro to Statistical Communication Theory* by John B. Thomas. Next, a comparator 92 compares the pulse output signal to a predetermined threshold that is typically slightly above the average noise of the system. If the pulse output signal is less than the threshold, the signal is ignored. If the pulse output signal is greater than the threshold, the signal is converted to a digital ON/OFF signal and sent to an AND gate 81. The AND gate 81 operates as follows: if both voltage signals are ON, the pulse output is ON; if both voltage signals are OFF, the pulse output is OFF; if only one voltage signal is ON, the pulse output is OFF. Thus an ON pulse output is generated only when two ON voltage signals are concurrently received at AND gate 81.

Figure 3:
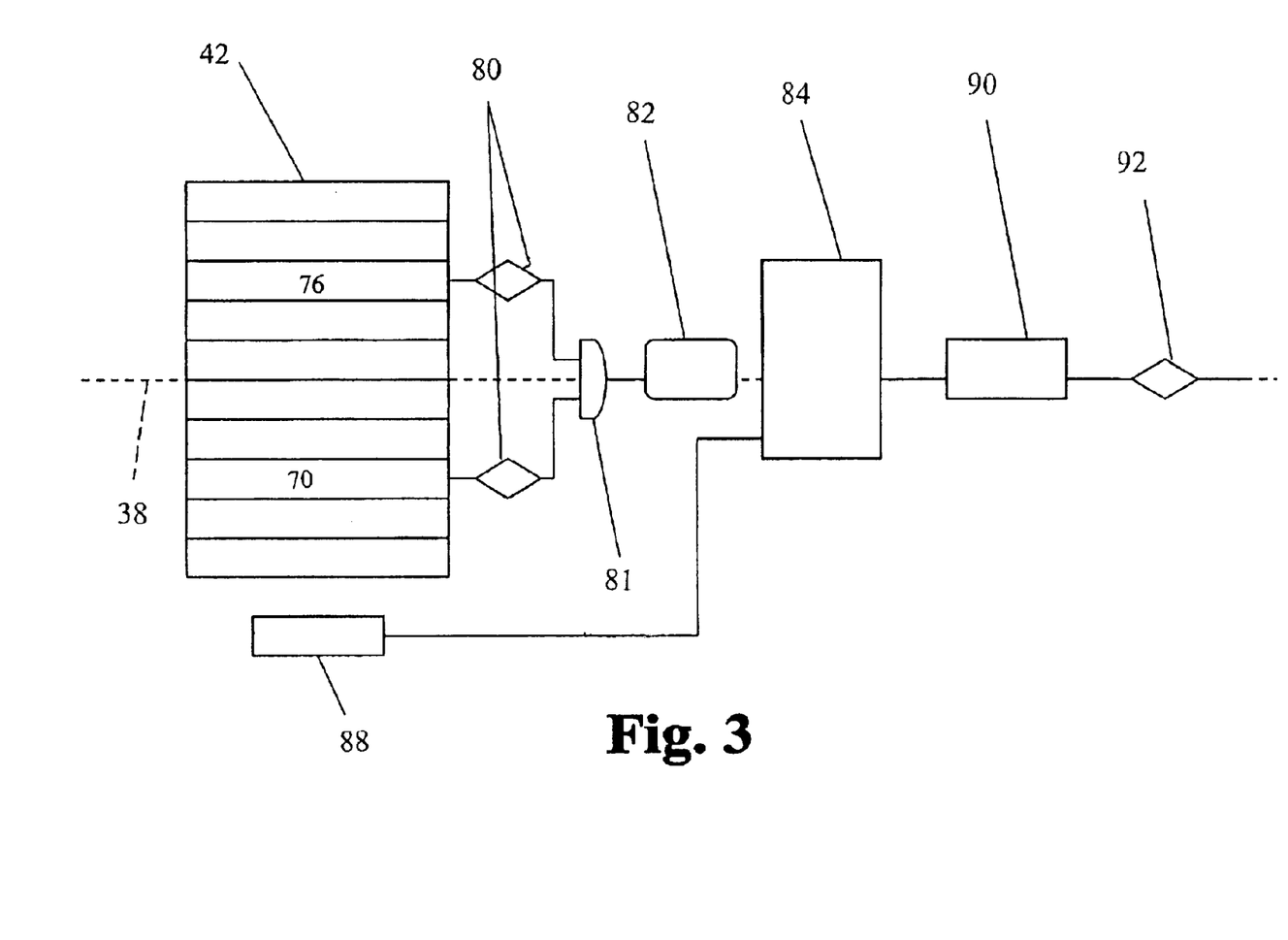
FIG. 3 is a schematic diagram of an alternative signal processing system for use with the particle detection system of the present invention.

As shown in FIG. 3, an alternative processing system of the present invention includes a transimpedance amplifier 80 that converts from electric current to voltage the pulse output signals generated by one of first and second detector elements 70 and 76 in photodetector array 42. Once the pulse output signals have been converted to voltage values, they are summed at one or more pulse summation amplifiers 82. As described above, background noise is canceled from the pulse output signal at a noise cancellation unit 84 that subtracts or divides a baseline noise pulse measured by a noise detector 88. Following noise cancellation, the pulse output signals are filtered by a filter 90, the shape of which is preferably similar to the shape the frequency response characteristic of the pulse output signal. Finally, a comparator 92 compares the pulse output signal to a predetermined threshold that is typically slightly above the average noise of the system. If the pulse output signal is less than the threshold, the signal is ignored. If the pulse output signal is greater than the threshold, the signal is processed by a computer (not shown) that measures voltage and determines particle size therefrom.

Figure 4:
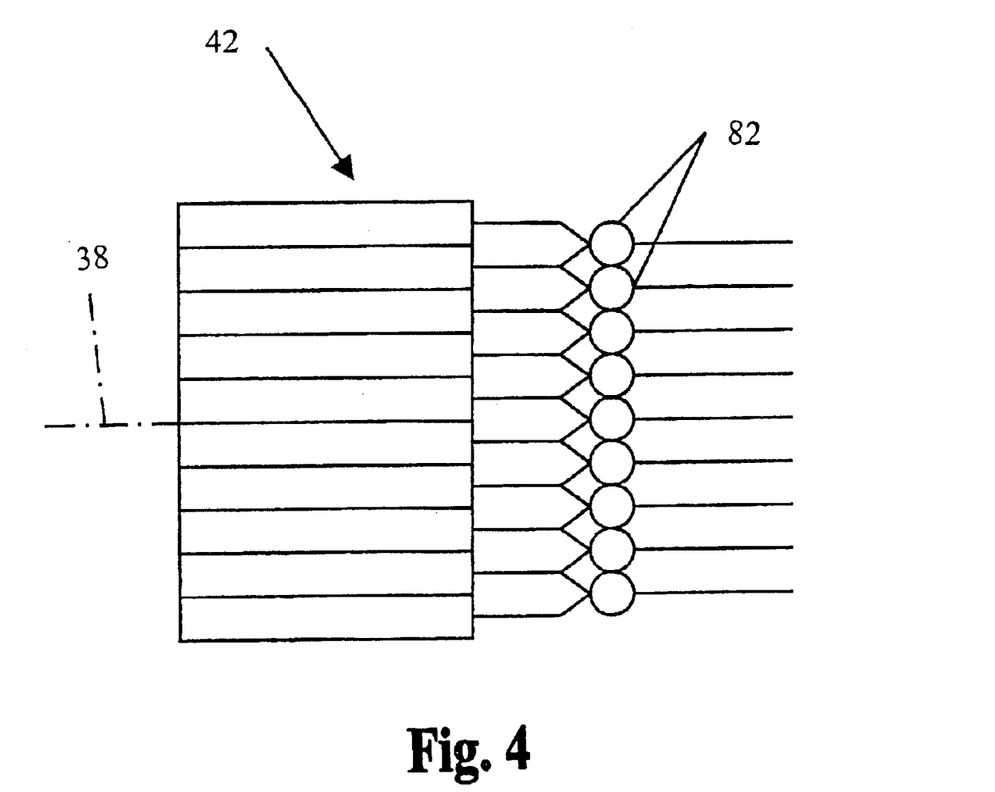
FIG. 4 is a schematic diagram of an alternative signal summation scheme for use with the particle detection system of the present invention.

An alternative signal summation scheme, shown in FIG. 4, entails summing at signal summation amplifiers 82 the pulse output signals of pairs of adjacent detector elements. This alternative signal summation scheme is preferably implemented in particle detection systems detecting large diameter particles for which the light beam propagating through view volume 26 is greater than the width of a single detector element in photodetector array 42. The signal summation scheme of FIG. 4 effectively doubles the width of each detector element in photodetector array 42, facilitating accurate detection of pulse output signals generated by large diameter particles. By summing the signals from adjacent detector elements, signal amplitude information and resolution are preserved.

Many signal processing systems are known to those skilled in the art. The above-described signal processing systems arc merely exemplary and, as skilled persons know, can be modified to achieve the objectives of the present invention. Such signal processing systems are within the scope of the present invention.

Figure 5:
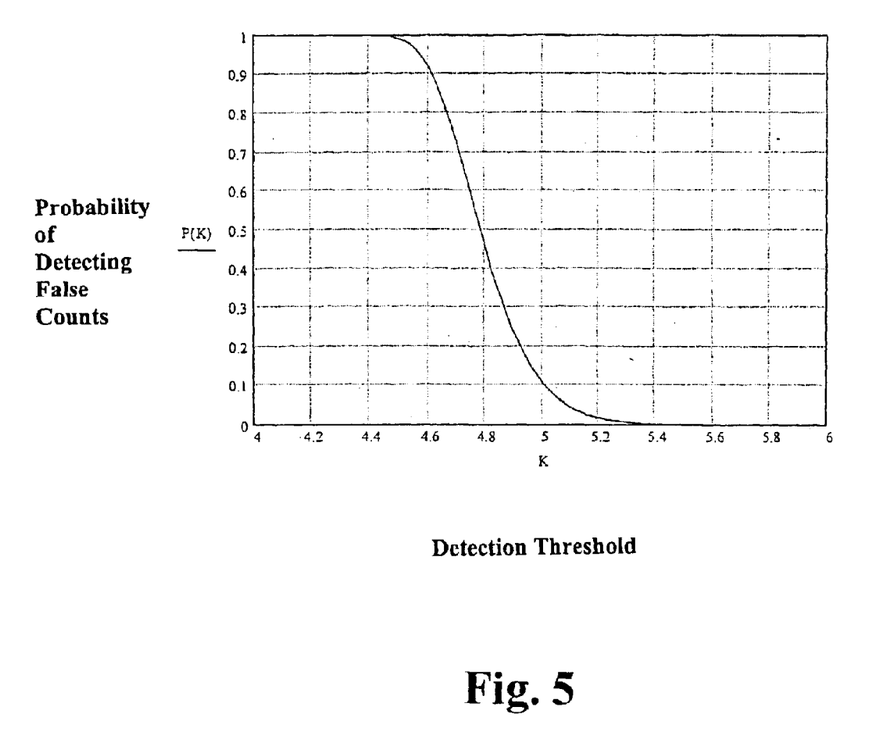
FIG. 5 is a graphical curve from which the probability of generating a minimum specified number of false predetermined particle counts during a predetermined time interval can be determined.

The preferred embodiments of the particle detection systems of the present invention have an increased ability to distinguish between noise and low-amplitude pulse output signals caused by small diameter particles. Signal enhancement results from the required temporal and spatial coincidence of pulse output signals. Because sample particles are counted only when both symmetrically opposed detector elements concurrently detect scattered light correlated components having a pulse output signal that exceeds a predetermined threshold, the incidence of randomly occurring noise pulses or excursions causing a false signal is significantly decreased. Specifically, the curve shown in FIG. 5 indicates that the probability that two pulse output signals will concurrently exceed the predetermined threshold is equal to the square of the probability that an individual pulse output signal will exceed the threshold. Consequently the threshold for a given false count rate may be lowered by more than a factor of the square root of two and still maintain the desired overall false count rate. Thus the coincidence function allows the use of a lower threshold setting without increasing the incidence of false particle signals, since most noise is random and is unlikely to concurrently trigger both detector elements of a symmetrically opposed pair. The use of a lower threshold facilitates more accurate detection of smaller diameter particles.

It will be obvious to those having skill in the art that many changes may be made to the details of the above-described embodiments of this invention without departing from the underlying principles thereof. The scope of the present invention should, therefore, be determined only by the following claims.

What is claimed is:

1. In a particle detection system for detecting sample particles entrained in a fluid stream, the particle detection system having a view volume that has an effective center and in which a light beam propagating along a light propagation path along an optical axis transversely intersects the fluid stream such that entrained particles upon which the light beam is incident scatter first and second correlated light components, the first light components scattered in first directions for propagation through a light collection lens system and incidence on a detector that produces signals representing the intensities of the first light components, and the second light components scattered in second directions that are different from the first directions, comprising:

a light reflector positioned relative to the effective center of the view volume to receive the second light components, the light reflector having light directing properties that cause reflections of the second light components in the form of corresponding inverted second light components that propagate through the view volume and the light collection lens system;

an array of first and second detector elements corresponding to spatial locations in the view volume of the entrained particles causing scattering of the first and second light components, the first detector elements being members of a first set of detector elements in the array and receiving the first light components and the second detector elements being members of a second set of detector elements in the array and receiving the corresponding inverted second light components, different pairs of the first and second detector elements in the respective first and second sets corresponding to different spatial locations along the light propagation path within the view volume and each of the different pairs producing detector pulse output signals representing the intensities of the first light component and its corresponding inverted second light component the pair received; and a signal processing system that responds to the detector pulse output signals by combining them to increase a detection system signal-to-noise ratio and thereby enhancing the detectability of the first and second light components to record presences of their corresponding particles entrained in the fluid stream.

2. The particle detection system of claim 1, in which the light reflector includes a curved mirror.

3. The particle detection system of claim 2, in which the curved mirror is of elliptical, aspherical, or spherical shape.

4. The particle detection system of claim 2, in which the curved mirror is of spherical or aspherical shape and has an optical center of curvature, the effective center of the view volume and center of curvature of the curved mirror being aligned with each other.

5. The particle detection system of claim 2, in which the curved mirror is of spherical shape and has a center of curvature and in which the light collection lens system has a collection system axis, the curved mirror and the light collection lens system positioned on opposite sides of the view volume with the center of curvature of the curved mirror centered on the collection system axis.

6. The particle detection system of claim 2, in which the curved mirror is of spherical shape and has a center of curvature and in which the light collection lens system has a collection system axis, the curved mirror and the light collection lens system positioned on opposite sides of the view volume with the center of curvature of the curved mirror centered on the optical axis.

7. The particle detection system of claim 1, in which the view volume is located within a flow chamber.

8. The particle detection system of claim 1, in which the signal processing system includes a comparator with a preset threshold and in which the combining of the detector pulse output signals includes determining whether signals corresponding to the pulse output signals produced by each of the different pairs of the first and second detector elements exceed the preset threshold.

9. The particle detection system of claim 1, in which the signal processing system includes multiple comparators with preset thresholds and in which the combining of the detector pulse output signals includes determining whether signals corresponding to the pulse output signals produced by each of the different pairs of the first and second detector elements, and exceeding the preset thresholds, are coincident in time.

10. The particle detection system of claim 9, in which detector pulse output signals that lack coincidence in time are rejected such that they are not processed by the signal processing system.

11. The particle detection system of claim 1, in which the signal processing system includes a pulse summation amplifier that sums coincident pulse output signals produced by each of the different pairs of the first and second detector elements.

12. In a particle detection system for detecting sample particles entrained in a fluid stream, the particle detection system having a view volume that has an effective center and in which a light beam propagating along a light propagation path along an optical axis transversely intersects the fluid stream such that entrained particles upon which the light beam is incident scatter first and second correlated light components, the first light components scattered in first directions for propagation through a light collection lens system having a collection system axis and for incidence on a detector that produces signals representing the intensities of the first light components, and the second light components scattered in second directions that are different from the first directions, comprising:

a light reflector positioned relative to the effective center of the view volume to receive the second light components, the light reflector having light directing properties that cause reflections of the second light components in the form of corresponding inverted second light components that propagate through the view volume and the light collection lens system;

an array of first and second detector elements corresponding to spatial locations in the view volume of the entrained particles causing scattering of the first and second light components, the first detector elements being members of a first set of detector elements in the array and receiving the first light components and the second detector elements being members of a second set of detector elements in the array and receiving the corresponding inverted second light components, each of multiple different pairs of the first and second detector elements in the respective first and second sets representing an opposing pair of detector elements that are positioned at equal distances from the collection system axis to view a common spatial location of the view volume by receiving concurrently the first and second light components propagating through the common spatial location and each of the different pairs producing detector pulse output signals representing the intensities of the first light component and its corresponding inverted second light component the pair received; and a signal processing system that responds to the detector pulse output signals by combining them to increase a detection system signal-to-noise ratio and thereby enhancing the detectability of the first and second light components to record presences of their corresponding particles entrained in the fluid stream.

13. The particle detection system of claim 12, in which the light reflector includes an inverting, retroreflecting device.

14. The particle detection system of claim 13, in which the inverting, retroreflecting device is a curved mirror.

15. The particle detection system of claim 13, in which the inverting, retroreflective device is of spherical or aspherical shape and has an optical center of curvature, the effective center of the view volume and center of curvature of the inverting, retroreflective device being aligned with each other.

16. The particle detection system of claim 13, in which the inverting, retroreflective device is of spherical shape and in which the inverting, retroreflective device and the fight collection lens system are positioned on opposite sides of the view volume with the center of curvature of the inverting, retroreflective device centered on the collection system axis.

17. The particle detection system of claim 13, in which the inverting, retroreflective device is of spherical shape and has a center of curvature and in which the light collection lens system has a collection system axis, the inverting, retroreflective device and the light collection lens system positioned on opposite sides of the view volume with the center of curvature of the inverting, retroreflective device centered on the optical axis.

18. The particle detection system of claim 12, in which the signal processing system includes multiple comparators with preset thresholds and in which the combining of the detector pulse output signals includes determining whether signals corresponding to the pulse output signals produced by each of the multiple different pairs of the first and second detector elements, and exceeding the preset thresholds, are coincident in time.

19. The particle detection system of claim 18, in which detector pulse output signals that lack coincidence in time are rejected such that they are not processed by the signal processing system.

* * * * *

UNITED STATES PATENT AND TRADEMARK OFFICE
CERTIFICATE OF CORRECTION

PATENT NO. : 6,784,990 B1
DATED : August 31, 2004
INVENTOR(S) : Richard K. DeFreez, James Brady and Kenneth L. Girvin

It is certified that error appears in the above-identified patent and that said Letters Patent is hereby corrected as shown below:

Column 6,
Line 42, "arc" should read -- are --

Column 10,
Line 3, "fight" should read -- light --

Signed and Sealed this

Eighteenth Day of January, 2005

JON W. DUDAS
*Director of the United States Patent and Trademark Office*